United States Patent [19]

Mark

[11] Patent Number: 4,558,703
[45] Date of Patent: Dec. 17, 1985

[54] VESTIBULAR STIMULATION METHOD

[76] Inventor: Hermann Mark, Fachartz fur Nals-Nasen-Ohrenhenheilkunde Favoritenstrasse 27, 1040 Wien 4, Austria

[21] Appl. No.: 497,679

[22] Filed: May 24, 1983

[30] Foreign Application Priority Data

May 27, 1982 [AT] Austria ................................. 2095/82

[51] Int. Cl.⁴ .............................................. A61N 1/36
[52] U.S. Cl. ................................................ 128/421
[58] Field of Search ................... 128/420 A, 421, 791, 128/793, 422

[56] References Cited

U.S. PATENT DOCUMENTS

| | | | |
|---|---|---|---|
| 1,679,245 | 7/1928 | Gaertner | 128/791 |
| 3,834,379 | 9/1974 | Grant | 128/791 |
| 3,881,495 | 5/1975 | Pannozzo et al. | 128/791 |
| 3,897,789 | 8/1975 | Blanchard | 128/422 |
| 3,908,669 | 9/1975 | Man et al. | 128/422 |
| 4,084,595 | 4/1978 | Miller | 128/422 |
| 4,147,171 | 4/1979 | Greene et al. | 128/421 |
| 4,148,321 | 4/1979 | Wyss et al. | 128/420 A |
| 4,331,163 | 5/1982 | Nomura | 128/793 |
| 4,340,063 | 7/1982 | Maurer | 128/421 |
| 4,372,319 | 2/1983 | Ichinomiya et al. | 128/422 |

OTHER PUBLICATIONS

Kenneth S. Cole, Membranes, Ions and Impulses, "A Chapter of Classical Biophysics", pp. 120–122.

*Primary Examiner*—Kyle L. Howell
*Assistant Examiner*—Ruth S. Smith
*Attorney, Agent, or Firm*—Cushman, Darby and Cushman

[57] ABSTRACT

An apparatus and method for treating a patient suffering from motion sickness such as air sickness and the like. The method includes the steps of applying electrodes to the vestibular area of the patient's head and providing current pulses in the current range of 0.5–3.8 mA, the pulses having a frequency in the range of 1–5 pulses per second and a pulse width in the range of 100–200 msec. The apparatus comprises a timing generator for determining pulse frequency, an impulse generator for generating a pulse waveform, an impulse former for controlling pulse shape and a driver stage for developing current pulses to be applied to the electrodes.

3 Claims, 1 Drawing Figure

VESTIBULAR STIMULATION METHOD

BACKGROUND OF THE INVENTION

This invention relates to the treatment of sea-sickness and similar maladies. More specifically, the invention provides a treatment method using vestibular stimulation.

SUMMARY OF THE INVENTION

It is an object of the invention to provide a method utilizing a small, easily portable and handy device for vestibular stimulation for treating sea-sickness and similar maladies. Such stimulation can provide relief from space sickness, air-sickness, dizziness and sea sickness. In essence, the invention provides this relief by producing in the afflicted person a sense of gravity acting on his limbs thereby providing a perception of "heaviness".

The vestibular stimulation apparatus according to the present invention applies a train of pulses to the patient's skull via electrodes placed in proximity thereto. It comprises in combination: a variable timing generator for controlling pulse frequency, a variable impulse generator for generating a series of impulses at the frequency of said timing generator, a variable impulse former for controlling the shape of the impulses and a variable driver stage for providing a signal to be applied to the electrodes. These elements are electrically connected to electrodes attachable, preferably in the skull area, to an afflicted patient. Power can be supplied either by a battery or from external power supply.

The invention provides to the patient a series of pulses that are substantially trapezoidal, in shape, or that the pulses are of a lasting even sequence, or that the pulses are delivered pulsatorily by the electrodes.

Moreover, the variable timing generator provides a frequency range that is variable between 1 and 5 pulses per second. The impulse generator is adjustable between 100 and 300 msec. The current provided by the driver stage is adjustable between 0.5 and 3.8 mA.

In addition the invention is characterized in that the variables are controlled by potentiometers. In the preferred embodiment the components of the device are modules being in effective connection with one another. The modules contain units, which are programmable and the individual modules are interconnected with one another via printed circuits.

The invention includes electrodes formed, in one embodiment, essentially in the manner of a bridge of a pair of eyeglasses. In an alternative configuration, the electrodes are applied to the patient by a headband holding them against the skull, preferably behind the ears. An alternative electrode carrier is a helmet. As yet another alternative, the electrodes can be implanted in or glued to the patient's skull area or the electrodes can be attached on the outside of the device and are connected with the device directly to the patient's body.

Above all in the case of space sickness, when the patient is in a gravity-less state, apparent conditions are to be created by this device according to the invention simulating the normal state in the gravitational zone of the earth. The simulated gravity feeling that the patient perceives protects him against avoidable physical and psychic disturbances, as they become effective in the gravity-less state through the loss of the body weight. For astronauts, the artificial sense of gravity would prevent the occurrence of space sickness and protects them against possible mistakes in handling and control caused thereby and having, in many cases irreparable consequences.

Furthermore, as a result of using the vestibular stimulation device according to the present invention, the pool of individuals available for space travel can be increased significantly. Those persons who because of susceptibility to nausea in a weightlessness state, for this reason alone had to be eliminated from space programs, can now be included as candidates for such programs.

The device according to the invention may also be used by persons suffering from sea sickness and dizziness and thus may serve a still considerably larger circle of humans. In addition any drug treatment with possible side effects will not be needed. The electrodes of the vestibular stimulation device according to the invention may be applied in the area of the skull by means of a headband, a hat, or as in the case of astronauts, by means of a helmet. The electrodes may also be integrated in the bridge of eyeglasses or they may be implanted below the skin in the body or attached on the skin, e.g. by glueing on or by means of suction cups. The current to be used is governed predominantly by the resistance of the skin and the degree of the affliction, but it lies within the approximate ranges of 0.5 to 3.8 mA. Preferably a trapezoidal pulse waveform is used, which is fed, for example, continuously evenly to the patient by way of wires coupled to the electrodes. All the pulse parameters can be adapted such as for example, the steepness of its edges or in its strength etc., to the patient. This may be accomplished for example, with a testing device, which throws out the necessary values and possibly even sends them to a minicomputer, having program chips with modules, which are contained in the possible modules of the device of the invention and thereby creates the best possible variant for a particular patient. The best results are achieved generally with a pulse duration of 100 to 300 msec., and a pulse frequency of 1 to 5 pulses per second.

The vestibular stimulation device of the invention may however, also be constructed as a homogenous circuit without modules. The desired pulse train parameters may be defined by the attending physician for example, by manipulating variable elements of the circuit such as for example potentiometers. At the same time the patient may be given a chance for self-regulation, which he may then carry out according to his need.

It is also an object of the present invention to provide a method for treating a patient afflicted with space sickness, air sickness, dizziness, sea sickness or the like comprising the steps of:
(a) applying electrodes to the patient;
(b) applying pulses of current through said electrodes; to the patient to provide vestibular stimulation, said pulses being in a frequency range of 1 to 5 pulses per second, the pulses having a pulse width in the range of 100–300 msecs., the current being in the range of 0.5–3.8 mA.

BRIEF DESCRIPTION OF THE DRAWING

The invention will be further described with reference to FIG. 1 (the sole figure) which is a schematic diagram of the vestibular stimulation device according to the present invention.

DETAILED DESCRIPTION OF THE DRAWING

Figure 1:
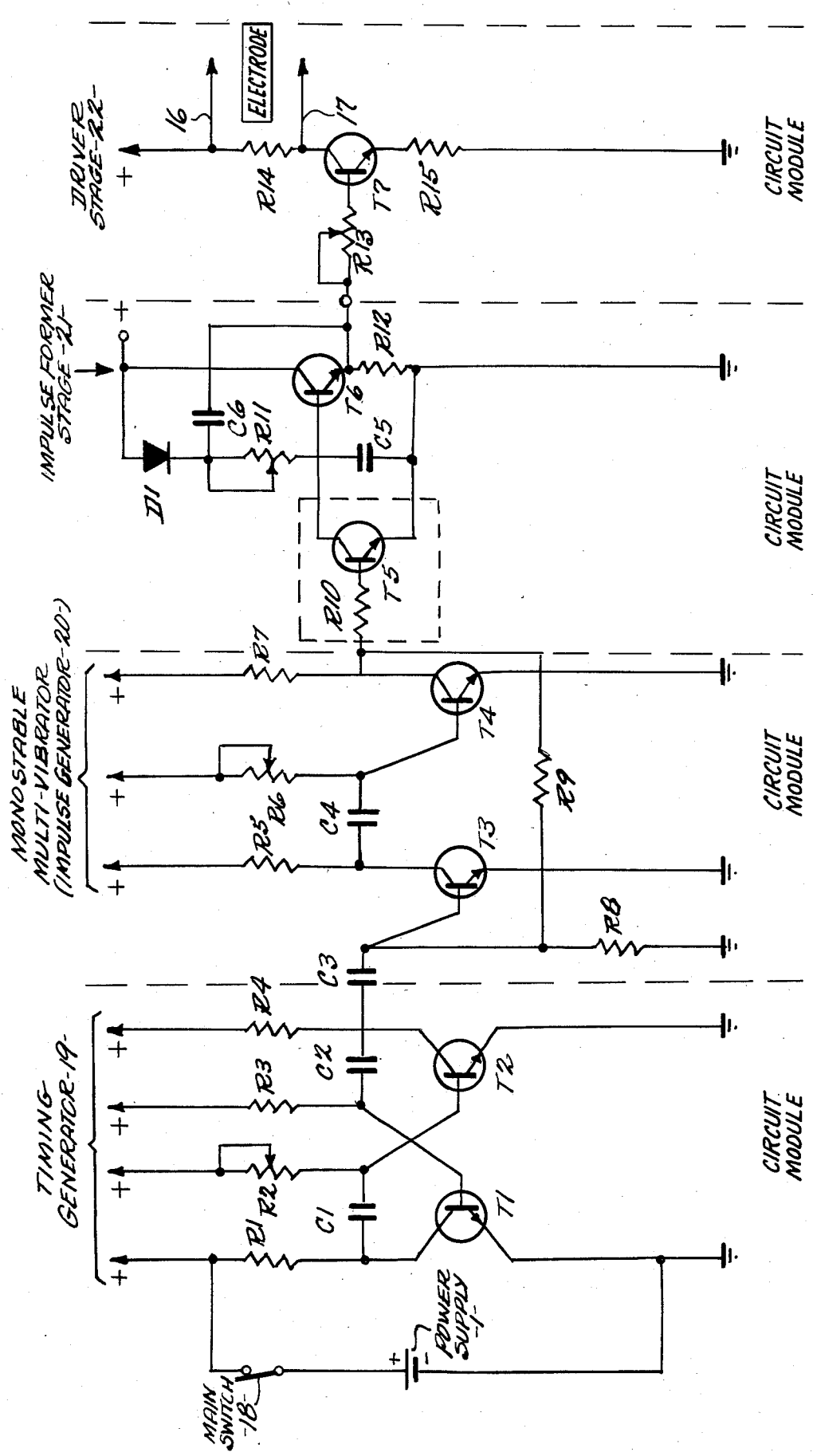

Referring to FIG. 1 (the sole figure) there is shown a preferred circuit diagram of the vestibular stimulation device of the invention. The device is powered by a power source 1 which represents either a battery or a power supply circuit coupled to a commercial power source. A main switch 18 couples power supply 1 to a timing generator 19. Transistor T1 and T2, resistances R1 to R4 and capacitors C1 and C2 constitute timing generator 19, the frequency of which may be controlled by controlling resistance R2, constituted by a potentiometer.

The voltage produced by the timing generator 19 is coupled by way of a capacitor C3 and triggers a monostable multivibrator 20 comprising transistors T3, T4 resistances R5 to R9 and capacitor C4, and which constitute the impulse generator. Resistance R6 is provided as a potentiometer, the resistance setting of which determines the duration pulses from impulse generator 20 (pulse width). The pulses produced by impulse generator 20 control a switching transistor T5 by way of resistance R10, which in turn controls an impulse former stage 21, comprising a transistor T6, resistances R11 and R12, capacitors C5 and C6 and a diode D1. Impulse-former stage 21 provides a trapezoidal pulse shape voltage signal responsive to the pulses produced by impulse generator 20, the flank steepness of which voltage signal may be controlled by setting resistance R11, implemented as a potentiometer. A variable resistance R13 determines the base current of the transistor T7 and thus the desired electrode voltage at the electrodes 16 and 17 which is produced in a driver stage 22 comprising a transistor T7 and resistances R14 and R15.

While the invention has been described in connection with what is presently considered to be the most practical and preferred embodiments, it is to be understood that the invention is not to be limited to the disclosed embodiments but on the contrary, it is intended to cover various modifications and equivalent arrangements included within the spirit and scope of the appended claims which scope is to be accorded the broadest interpretation so as to encompass all such modifications and equivalent structures.

I claim:

1. A method for treating a patient afflicted with space sickness, air sickness, dizziness, sea sickness or the like comprising the steps of:
   (a) applying electrodes to the patient;
   (b) applying pulses of current through said electrodes to the patient to stimulate the patient's vestibular nerve, said pulses being in a frequency range of 1 to 5 pulses per second, the pulses having a pulse width in the range of 100–300 msecs., the current being in the range of 0.5–3.8 mA.

2. A method according to claim 1 wherein the step of applying electrodes comprises the step of applying electrodes to the vestibular area of the patient's head.

3. A method according to claim 1 wherein the step of applying current pulses comprises the step of applying current pulses that are substantially trapezoidal in shape.

* * * * *